United States Patent [19]

Rounbehler et al.

[11] Patent Number: 5,567,623
[45] Date of Patent: Oct. 22, 1996

[54] METHOD AND SYSTEM FOR SAMPLING AND DETERMINING THE PRESENCE OF COMPOUNDS

[75] Inventors: David P. Rounbehler, Bedford; David H. Fine, Sudbury; Eugene K. Achter, Lexington, all of Mass.; Stephen J. MacDonald, Salem, N.H.; Daniel B. Dennison, Kennesaw, Ga.

[73] Assignee: The Coca-Cola Company, Atlanta, Ga.

[ * ] Notice: The term of this patent shall not extend beyond the expiration date of Pat. No. 5,470,754.

[21] Appl. No.: 416,574

[22] Filed: Apr. 4, 1995

Related U.S. Application Data

[60] Division of Ser. No. 20,804, Feb. 22, 1993, Pat. No. 5,470,754, which is a continuation-in-part of Ser. No. 890,863, Jun. 1, 1992, Pat. No. 5,352,611, and a continuation-in-part of Ser. No. 890,864, Jun. 1, 1992.

[51] Int. Cl.$^6$ .................................................. G01N 21/76
[52] U.S. Cl. ................. 436/158; 436/106; 436/139; 436/159; 436/160; 436/152; 436/172; 422/78; 422/80; 422/82.08; 422/93; 422/98
[58] Field of Search .................... 436/106, 108, 436/111–113, 116, 117, 118, 139, 140, 172, 158, 159, 160, 152–153, 52, 53; 422/78, 80, 83, 93, 98, 82.08

[56] References Cited

U.S. PATENT DOCUMENTS

| | | |
|---|---|---|
| 3,533,744 | 10/1970 | Unger . |
| 3,763,877 | 10/1973 | Lieb . |
| 3,845,309 | 10/1974 | Helm et al. . |
| 3,870,468 | 3/1975 | Neti .............................. 436/116 |
| 4,157,777 | 6/1979 | Dymond et al. . |
| 4,193,963 | 3/1980 | Bruening et al. ................ 422/52 |
| 4,265,855 | 5/1981 | Mandle et al. . |
| 4,580,440 | 4/1986 | Reid et al. . |
| 4,761,268 | 8/1988 | Andersen et al. . |
| 4,775,633 | 10/1988 | Roundbeller ..................... 436/106 |
| 4,830,192 | 5/1989 | Plester et al. . |
| 4,843,016 | 6/1989 | Fine ................................ 436/106 |
| 4,858,768 | 8/1989 | Plester . |
| 4,880,120 | 11/1989 | Myers et al. . |
| 4,899,573 | 2/1990 | Dimmick et al. . |
| 4,909,089 | 3/1990 | Achter et al. . |
| 4,909,090 | 3/1990 | McGown et al. . |
| 5,067,616 | 11/1991 | Plester et al. . |
| 5,096,834 | 3/1992 | Saito . |
| 5,108,705 | 4/1992 | Rounbehler et al. . |
| 5,152,963 | 10/1992 | Wreyford ........................ 422/93 |
| 5,255,072 | 10/1993 | Mikasa et al. ................... 422/93 |

*Primary Examiner*—James C. Housel
*Assistant Examiner*—Rachel Heather Freed
*Attorney, Agent, or Firm*—Birch, Stewart, Kolasch & Birch, LLP

[57] ABSTRACT

A system and method are provided for minimizing the effects of background signals in masking signals indicating the presence of substances to be detected such as contaminants in materials moving rapidly along a conveyor. The contaminants detected may include nitrogen containing compounds and hydrocarbons. The system and method of the present invention minimizes the number of falsely positive indications of the presence of such substances due to background signals and changes in background signals. The substances detected are divided into first and second sample portions and the respective portions are heated. The first heated portion is reacted with ozone to generate radiation by chemiluminescence having characteristic wavelengths related to substances in the first portion. The second portion heated is also reacted with ozone to generate radiation by chemiluminescence having characteristic wavelengths related to substances in the second portion. The radiation of the respective first and second portions is selectively detected. The heating and detecting steps are performed in a manner so as to yield a higher level of detected radiation from one of the portions of the sample then the other for at least some of the selected compounds being detected. Electrical signals from the respective first and second portions are generated and compared in order to determine the presence or absence of selected compounds in the sample. Appropriate reject signals for a bottle sorting system are generated accordingly.

16 Claims, 5 Drawing Sheets

METHOD AND SYSTEM FOR SAMPLING AND DETERMINING THE PRESENCE OF COMPOUNDS

BACKGROUND OF THE INVENTION

This application is a divisional application of Ser. No. 08/020,804 filed Feb. 22, 1993, now U.S. Pat. No. 5,470,754, which is a continuation-in-part of application Ser. Nos. 07/890,863 filed Jun. 1, 1992, now U.S. Pat. Nos. 5,352,611 and 07/890,864 filed Jun. 1, 1992, both of which are assigned to the same assignee as the present invention.

The present invention relates to an inspection system for sampling and determining the presence of certain substances, such as residues of contaminants within containers such as glass or plastic bottles. More specifically, the present invention relates to an improved sampling and analyzing system and method for determining the presence of substances such as residues of contaminants, as in containers such as beverage bottles rapidly moving along a conveyor past a test station in a container sorting system.

In many industries, including the beverage industry, products are packaged in containers which are returned after use, washed and refilled. Typically refillable containers, such as beverage bottles, are made of glass which can be easily cleaned. These containers are washed and then inspected for the presence of foreign matter.

Glass containers have the disadvantage of being fragile and, in larger volumes, of being relatively heavy. Accordingly, it is highly desirable to use plastic containers because they are less fragile and lighter than glass containers of the same volume. However, plastic materials tend to absorb a variety of organic compounds which may later be desorbed into the product thereby potentially adversely affecting the quality of the product packaged in the container. Examples of such organic compounds are nitrogen containing compounds such as ammonia, organic nitrogen compounds, and hydrocarbons including gasoline and various cleaning fluids.

The aforementioned U.S. Pat. No. 5,352,611 discloses a system and method for detecting the presence of these nitrogen containing and hydrocarbon compounds using a chemiluminescence analyzer. That system and method works quite well, but improvements are desirable to overcome interferences which may occasionally cause difficulties in achieving desired sensitivity and accuracy of detection. Such interferences result from background signals which may mask detection of low levels of certain compounds and whose variation with time may also result in false positives (and thus unwarranted rejection of uncontaminated containers). Accordingly, a need in the art exists for a chemiluminescence analyzer with improved accuracy and sensitivity.

SUMMARY OF THE INVENTION

Accordingly, it is a primary object of the present invention to provide a method and system for detecting the presence or absence of specific substances—e.g., contaminants such as nitrogen containing compounds and hydrocarbons, in materials as the materials move rapidly along a conveyor with improved accuracy which minimizes the deleterious effects of background signals.

It is a particular object of the invention to minimize the effects of background signals in masking signals indicating the presence of such substances to be detected.

It is another particular object of the invention to minimize, during detection of the presence or absence of such substances, the number of falsely positive indications of the presence of such substances due to background signals and changes in background signals.

The objects of the present invention are fulfilled by providing a method comprising the steps of:

collecting a sample;

dividing the sample into first and second portions;

heating the first portion of the sample to a first temperature;

heating the second portion of the sample to a second temperature;

mixing the heated first portion of the sample with ozone to cause a chemical reaction therewith in order to generate radiation by chemiluminescence having characteristic wavelengths related to substances in said first portion;

mixing the heated second portion of the sample with ozone to cause a chemical reaction therewith in order to generate radiation by chemiluminescence having characteristic wavelengths related to substances in said second portion;

selectively detecting radiation emitted by chemiluminescence from the first portion of the sample;

selectively detecting radiation emitted by chemiluminescence from the second portion of the sample;

said heating and detecting steps being performed in a manner so as to yield a higher level of detected radiation from one of said portions of the sample than the other for at least some of the selected compounds;

generating first electrical signals from the radiation selectively detected from the first portion of the sample and second electrical signals from the radiation selectively detected from the second portion of the sample; and comparing the first electrical signals with the second electrical signals in order to determine the presence or absence of selected compounds in the sample;

said heating, mixing, detecting, and generating, steps for said first portion being performed at essentially the same time as said heating, mixing, detecting, and generating steps for said second portion, and said comparing step being performed in a manner so as to cancel background signals in said portions.

In a preferred embodiment heating of the first portion is performed in a first converter having a ceramic heating chamber and heating of the second portion is performed in a second converter having nickel materials in its heating chamber. Therefore, the respective first and second sample portions are oxidized in different chemical environments. The radiation generated by chemiluminescence of the sample in the ceramic converter is passed through a quartz filter and detected. The radiation generated by chemiluminescence of the sample in the nickel converter is passed through a red (infrared) filter and detected. The signal related to radiation passing through the quartz filter is subtracted from the signal related to the radiation passing through the red filter by a computer. The result is compared to certain predetermined threshold criteria to determine the presence or absence of certain nitrogen or hydrocarbon compounds of interest. Appropriate reject signals for a bottle sorting system are generated accordingly.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limiting of the present invention and wherein.

DETAILED DESCRIPTION OF PREFERRED EMBODIMENTS

The disclosures of the aforementioned applications Ser. Nos. 07/890,863 and 07/890,864 are incorporated herein by reference.

Figure 1:
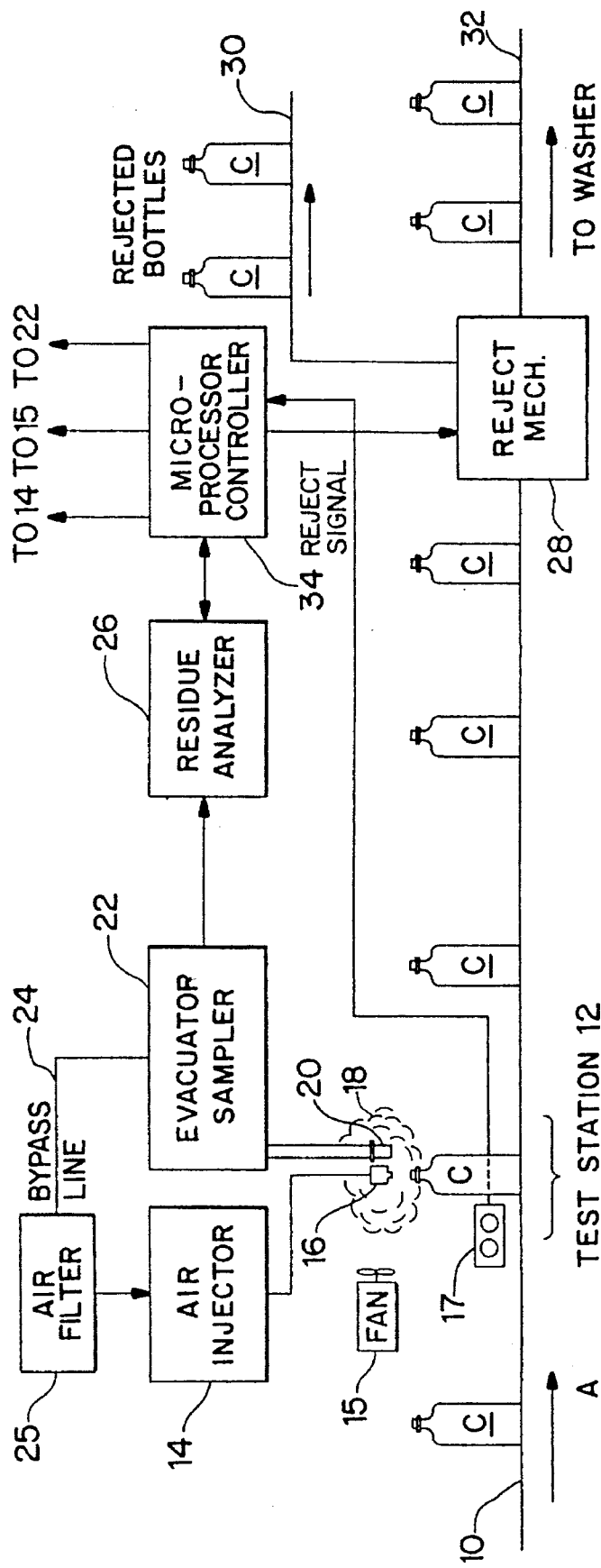
FIG. 1 is a schematic block diagram of the sampling and residue analyzing system disclosed in U.S. Pat. No. 5,352,611 illustrating a plurality of containers moving seriatim along a conveyor system through a test station, reject mechanism and washer station.

With reference to FIG. 1 of parent application Ser. No. 07/890,863, there is illustrated a conveyor 10 moving in the direction of arrow A having a plurality of uncapped, open-topped spaced containers C (e.g., plastic beverage bottles of about 1500 c.c. volume) disposed thereon for movement seriatim through a test station 12, reject mechanism 28 and conveyor 32 to a washer system. To achieve higher test rates containers C could be touching each other rather than spaced. The contents of containers C would typically include air, volatiles of residues of contaminants, if any, and volatiles of any products such as beverages which had been in the containers. An air injector 14 which is a source of compressed air is provided with a nozzle 16 spaced from, but aligned with, a container C at test station 12. That is, nozzle 16 is disposed outside of the containers and makes no contact therewith. Nozzle 16 directs compressed air into containers C to displace at least a portion of the contents of the container to thereby emit a sample cloud 18 to a region outside of the container being tested.

As an alternative to compressed air, $CO_2$ gas could be utilized as the injected fluid. Also, the compressed air or $CO_2$ gas could be heated to enhance volatility of the compounds being tested.

The column of air injected through nozzle 16 into a container C would be typically of the order of about 10 c.c. for bottle speeds of about 200 to 1000 bottles per minute. A rate of 400 bottles per minute is preferable and is compatible with current beverage bottle filling speeds. The desired test rate may vary with the size of the bottles being inspected and filled. Of course the bottles could be stationary or moving slower than 200 bottles per minute and the system would still work. Only about 10 c.c. of the container contents would be displaced to regions outside of the bottle to form sample cloud 18.

Also provided is an evacuator sampler 22 which may comprise a vacuum pump or the like coupled to a sampling tube or conduit 20. The tube is mounted near, and preferably downstream (e.g., about $\frac{1}{16}$ inch) of the air injector 14 so as to be in fluid communication with sample cloud 18 adjacent to the opening at the top of containers C.

Neither nozzle 16 nor tube 20 contacts the containers C at test station 12; rather both are spaced at positions outside of the containers in close proximity to the openings thereof. This is advantageous in that no physical coupling is required to the containers C, or insertion of probes into the containers, which would impede their rapid movement along conveyor 10 and thus slow down the sampling rate. High speed sampling rates of from about 200 to 1000 bottles per minute are possible with the system and method of the present invention. The conveyor 10 is preferably driven continuously to achieve these rates without stopping or slowing the bottles down at the test station.

A bypass line 24 is provided in communication with the evacuator sampler 22 so that a predetermined portion (preferably about 90%) of the sample from cloud 18 entering tube 20 can be diverted through bypass line 24. The remaining sample portion passes to a residue analyzer 26, which determines whether specific substances are present, and then is exhausted. One purpose of diverting a large portion of the sample from cloud 18 is to reduce the amount of sample passing from evacuator sampler 22 to residue analyzer 26 in order to achieve high speed analysis. This is done in order to provide manageable levels of samples to be tested by the residue analyzer 26. Another purpose for diverting a portion of the sample is to be able to substantially remove all of sample cloud 18 by evacuator 22 from the test station area and divert the excess through bypass line 24. In a preferred embodiment the excess portion of the sample passing through bypass line 24 returned to air injector 14 for introduction into the subsequent containers moving along conveyor 10 through nozzle 16. However, it would also be possible to simply vent bypass line 24 to the atmosphere.

It should be understood that sample cloud 18 could be analyzed in situ without transporting it to a remote analyzer such as 26. It could also be transported to analyzer 26 by blowing rather than sucking.

A microprocessor controller 34 including an analog to digital converter is provided for controlling the operation of air injector 14, evacuator sampler 22, residue analyzer 26, a reject mechanism 28 and an optional fan 15. Container sensor 17 including juxtaposed radiation source and photodetector is disposed opposite a reflector (not shown) across conveyor 10. Sensor 17 tells controller 34 when a container arrives at the test station and briefly interrupts the beam of radiation reflected to the photodetector. Optional fan 15 is provided to generate an air blast towards sample cloud 18 and preferably in the direction of movement of containers C to assist in the removal of sample cloud 18 from the vicinity of test station 12 after each container C is sampled. This clears out the air from the region of the test station so that no lingering residues from an existing sample cloud 18 can contaminate the test station area when successive containers C reach the test station for sampling. Thus, sample carryover between containers is precluded. The duty cycle for operation of fan 15 is controlled by microprocessor 34 as indicated diagrammatically in FIG. 1. Preferably fan 15 is continuously operating for the entire time the rest of the system is operating.

A reject mechanism 28 receives a reject signal from microprocessor controller 34 when residue analyzer 26 determines that a particular container C is contaminated with a residue of various undesirable types. Reject mechanism 28 diverts contaminated rejected bottles, as to a conveyor 30, and allows passage of uncontaminated, acceptable bottles to a washer (not shown) on a conveyor 32.

An alternative option is to place the bottle test station downstream of the bottle washer in the direction of conveyor travel, or to place an additional test station and sample and residue analyzing system after the washer. In fact it may be preferable to position the test station and system after the washer when inspecting bottles for some contaminants. For example, if the contaminant is a hydrocarbon, such as gasoline which is insoluble in water, it is easier to detect residues of hydrocarbons after the bottles have been washed. This is because during the washing process in which the bottles are heated and washed with water, water soluble chemical volatiles are desorbed from the bottles by the heating thereof and then dissolved in the washing water. Certain hydrocarbons, on the other hand, not being water soluble, may then be sampled by a sampler 22 downstream of the washer, to the exclusion of the dissolved, water-soluble chemicals. Therefore, the detection of such hydrocarbons can be performed without potential interference from other water soluble chemicals if the bottles pass through a washer before testing.

Referring to FIG. 2 there is illustrated a specific embodiment of a detector system for use with the sampling and analyzing system of FIG. 1 wherein like reference numerals refer to like parts. The detector system of FIG. 2 is also fully disclosed in parent application Ser. No. 07/890,863 filed Jun. 1, 1992. As illustrated, a nozzle 16 is provided for generating an air blast which passes into a container (not shown) being inspected. The air passing through nozzle 16 may be heated or unheated, it being advantageous to heat the air for some applications. Juxtaposed to the nozzle 16 is sample inlet tube 20 including a filter 40 at the output thereof for filtering out particles from the sample. Suction is provided to tube 20 from the suction side of pump 82 connected through a detector assembly 27.

A portion of the sample (for example, 90–95% of a total sample flow of about 6000 c.c. per minute), as described in connection with FIG. 1, is diverted through a bypass line 24 by means of connection to the suction side of a pump 46. Pump 46 recirculates the air through an accumulator 48, a normally open blast control valve 50, and back to the air blast output nozzle 16. A backpressure regulator 54 helps control pressure of the air blast through nozzle 16 and vents excess air to exhaust 57. Blast control valve 50 receives control signals through line 50A from microprocessor controller 34 to normally maintain the valve open to permit the flow of air to the nozzle.

Electrical power is provided to pump 46 via line 46A coupled to the output of circuit breaker 76 which is in turn coupled to the output of AC filter 74 and AC power supply PS.

The detector assembly 27 in the embodiment of FIG. 2 is an analyzer which detects the residue of selected compounds such as nitrogen containing compounds in the containers being inspected by means of a method of chemiluminescence. This type of detector is generally known and includes a chamber for mixing ozone with nitric oxide, or with other compounds which react with ozone, in order to allow them to react, a radiation-transmissive element (with appropriate filter), and a radiation detector to detect chemiluminescence from the products of reaction. For example, when NO, produced from heating nitrogen compounds (such as ammonia) in the presence of an oxidant (e.g. oxygen in air), chemically reacts with the ozone, characteristic light emission is given off at predetermined wavelengths such as wavelengths in the range of about 0.6 to 2.8 microns. Selected portions of the emitted radiation of chemiluminescence, and its intensity, can be detected by a photomultiplier tube.

Accordingly, in the system of FIG. 2 ambient air is drawn in through intake 60 and air filter 62 to an ozone generator 64. Ozone is generated therein, as by electrical discharge into air, and is output through ozone filter 66 and flow control valve 68 to the detector assembly 27 wherein it is mixed with samples from containers input through intake tube 20, filter 40, flow restrictor 42, and converter 44. The sample from intake tube 20 is passed through a converter 44, such as an electrically-heated nickel tube, in which the temperature is raised to approximately 800° C. to 1000° (e.g., about 900° C.) before being input to detector assembly 27. Temperatures in the range of 400° C. to 1400° C. may also be acceptable. When nitrogen-containing compounds such as ammonia are so heated, NO (nitric oxide) is produced, and the nitric oxide is supplied to the chamber of the detector assembly 27. Compounds other than NO which may react with $O_3$ and chemiluminescence may also be produced in converter 44 e.g., organic compounds derived from heating of gasoline, kerosene, or cleaning residue.

A temperature controller 70 supplied with electrical power through a transformer 72 is used to control the temperature of converter 44.

The samples in the detector assembly 27 after passage through its chamber are output through an accumulator 85 and pump 82 to an ozone scrubber 56, and to an exhaust output 57 in order to clear the residue detector for the next sample from the next container moving along the conveyor 10 of FIG. 1. (As indicated above, an (optional) fan, not shown in FIG. 2, may be employed to help clear any remaining sample cloud from near the sample inlet tube 20.) Outputs from detector assembly 27 relating to the results of the tests are output through a preamp 84 to microprocessor 34 which feeds this information in an appropriate manner to a recorder 83. The recorder 83 is preferably a conventional strip recorder, or the like, which displays signal amplitude vs. time of the sample being analyzed.

The microprocessor 34 may be programmed to recognize, as a "hit" or the detection of a specific residue, a signal peak from a photodetector of the detector assembly 27 which is present in a predetermined time interval (based on the sensed arrival of a container at the test station) and whose slope and amplitude reach predetermined magnitudes and thereafter maintain such levels for a prescribed duration.

The microprocessor controller 34 also has an output to a bottle ejector 28 to reject contaminated bottles and separate them from bottles en route to a washer.

A calibration terminal 86 is provided for residue analyzer 27 for adjusting the high voltage supply 26A associated with the detector assembly. Also provided is a recorder attenuator input terminal 88 connected to the microprocessor controller 34 for adjusting the operation of the recorder. Detector assembly 27 receives electrical power from the high voltage supply 26A.

Additional controls include operator panel 90 including a key pad and display section permitting an operator to control the operation of the detector assembly 27 in an appropriate fashion.

DC power is supplied to all appropriate components through DC power supply 78 coupled to the output of power supply PS.

An optional alarm enunciator 80A is provided for signaling an operator of the presence of a contaminated container. Alarm enunciator 80A is coupled to the output of microprocessor controller 34 via output control line 80C. A malfunction alarm 80B is also coupled to microprocessor controller 34 for receiving fault or malfunction signals such as from pressure switch 58 or vacuum switch 87 when pressures are outside of certain predetermined limits.

Other safety devices may be provided such as vacuum gauge 89, and back pressure control valve 54 for ensuring proper operation of the system.

Figure 2:
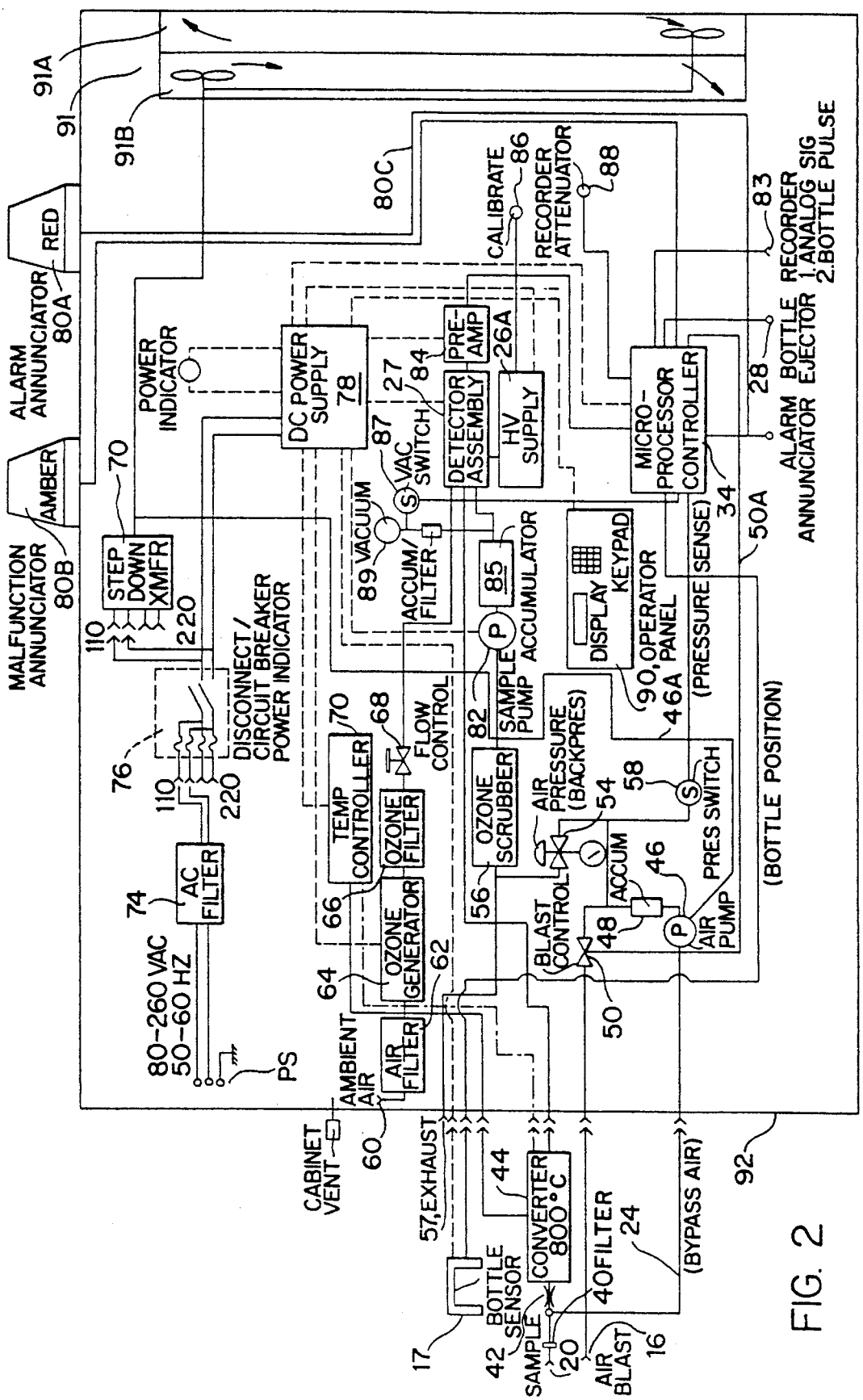
FIG. 2 is a block diagram also disclosed in U.S. Pat. No. 5,352,611 illustrating a possible implementation of the system of FIG. 1 in a detector system in which the contaminant being detected may be a nitrogen containing compound.

Most components of the entire system of FIG. 2 are preferably enclosed in a rust-proof, stainless steel cabinet 92. The cabinet is cooled by a counter-flow heat exchanger 91 having hermetically separated sections 91A and 91B in which counter air flow is provided by appropriate fans.

The system illustrated in FIG. 2 has a single detector assembly 27 for analyzing the sample evacuated into tube 20 and converter or converter 44. In most instances this system works quite well to detect either hydrocarbons or nitrogen containing compounds. However, sometimes a signal of interest may be hidden, or masked by background NOx (NO or $NO_2$) signals. Also, background signals, particularly during periods of rapid variation in background, may result in an indication that a compound of interest is present even though the compound is absent—i.e., a "false positive". Background NOx could vary due to passage of a fork-lift truck in the plant in the vicinity of the testing apparatus; due to different atmospheres in which some of the bottles to be tested were stored; or due to traffic outside of the plant and other various causes.

Figure 3:
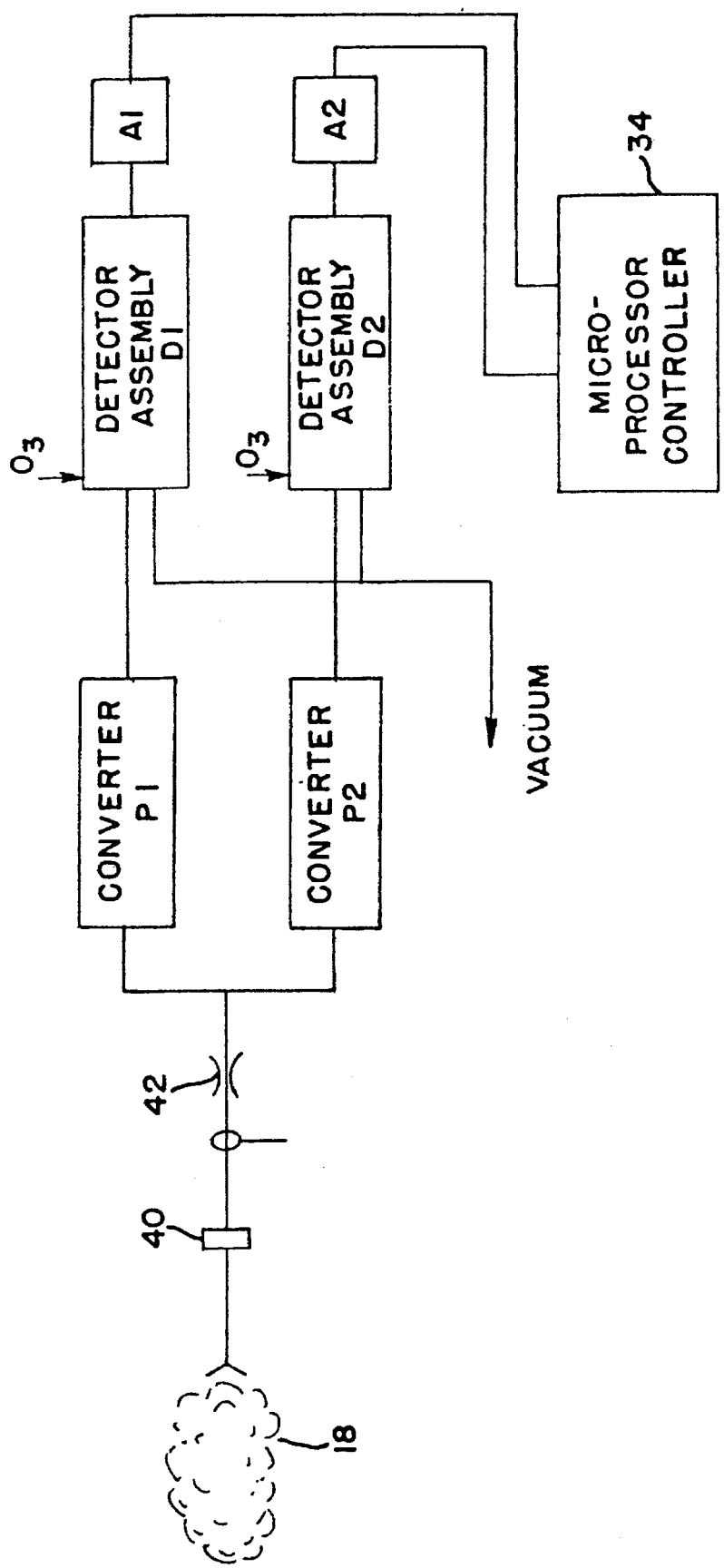
FIG. 3 is a schematic diagram of an improved analyzer system according to the present invention.

In order to avoid false positives and to keep signals of interest from being hidden in background signals, a preferred embodiment of the present invention includes an improved sample analyzer system, portions of which are illustrated in FIG. 3. The system is similar in many respects to that of FIG. 2; however, converter 44, detector assembly 27, and preamp 84 of the FIG. 2 system are replaced by the components shown in FIG. 3.

With reference in detail to FIG. 3, a sample such as from sample cloud 18 emerging from a container to be inspected is evacuated into sample tube 20 and passes through filter 40 and flow restrictor 42. The sample is then split into two parallel flow lines connected to parallel converters P1, P2. Converter P1 is preferably a ceramic converter so that the portion of the sample being heated therein is heated in the presence of ceramic materials. Converter P2 is preferably a nickel converter (formed of or containing nickel) so that the portion of the sample being heated therein is heated in the presence of nickel oxide. The output of container P1 is connected to the input of a chemiluminescence detector assembly D1 and the output of the nickel converter P2 is connected to the input of a chemiluminescence detector assembly D2. Chemiluminescence detector assembly D1 is provided with a quartz output filter—e.g., a 0.19 micron cutoff filter—so that radiation of wavelengths greater than 0.19 microns emitted by chemiluminescence within detector assembly D1 passes through the quartz filter to a photomultiplier tube which converts the radiation signal into an electrical signal having a characteristic shape and amplitude for each substance to be detected at characteristic wavelengths for the respective substances. The radiation emitted is generated by the chemical reaction of the sample in the detector with ozone gas supplied thereto in a manner which is well known in the art. In other words, detector assembly D1 detects the presence of substances which emit characteristic wavelengths of radiation which will pass through a quartz filter.

Detector assembly D2, on the other hand, has an infrared output filter—e.g. a 0.6 micron cut-off filter—which will selectively pass radiation in the infrared (and longer wavelength) region of the spectrum corresponding to various nitrogen containing compounds.

In operation, a sample from cloud 18 is sucked through sample tube 20, filter 40, and flow restrictor 42 and is split into approximately equal portions to pass into and through the two converters P1, P2 arranged in parallel. Both converters P1 and P2 are heated to approximately 900° C. A temperature of 900° C. is preferable, however, the system will achieve satisfactory results if the converters are heated to substantially the same temperature in the range of approximately 800° C. to 1400° C.

As stated above, converter P1 is a ceramic converter whose reaction chamber is lined with, a material such as aluminum oxide or the like. The other converter P2 is made of or contains nickel, e.g. converter P2 is a nickel alloy tube or a ceramic tube containing a nickel wire coil.

Typical dimensions for the converters P1 and P2 are approximately 15" long; 0.03–0.2" inside diameter; and typically ⅛" inside diameter, ¼" outside diameter.

Detectors D1 and D2 are coupled to the outlets of the respective converters P1 and P2 and to a vacuum in order to draw the sample through the converters and the detectors. The outputs of the detectors D1 and D2 are connected through suitable amplifiers A1 and A2 to a microprocessor controller 34, which includes analog to digital converters and is operable to process the electrical signals S1 and S2 produced by the detectors D1 and D2 and provide outputs which include individual processed signals and a net signal which results from the subtraction of signals output from the respective detectors—e.g., a net signal (S2–S1).

Preferably, the flow resistance through converters P1 and P2, detectors D1 and D2, and flow lines associated with these components is designed to be relatively equal so that timewise variation of background is the same as measured by detectors D1 and D2. The main flow resistance (and hence flow rate) is set by the flow restrictor 42.

Figure 4:
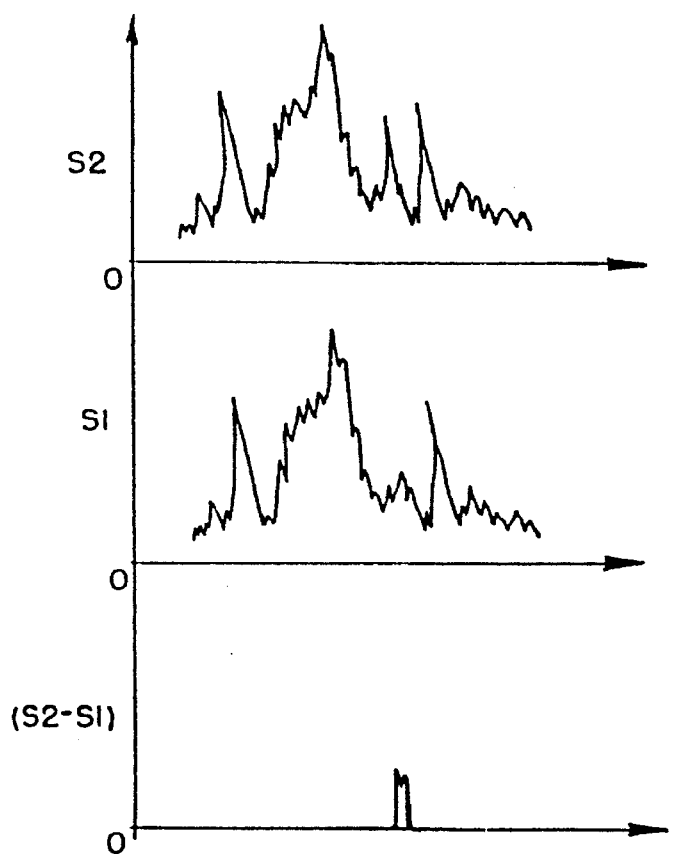
FIG. 4 illustrates graphs of signals detected and processed by the system of FIG. 3 for a sample having nitrogen containing compounds such as $NH_3$.
Figure 5:
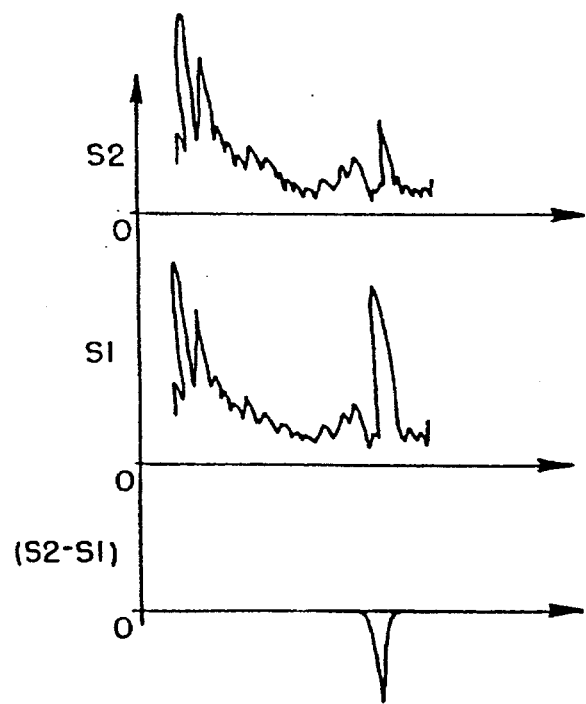
FIG. 5 illustrates graphs of signals detected and processed by the system of FIG. 3 for a sample containing hydrocarbons such as diesel fuel or kerosene.
Figure 6:
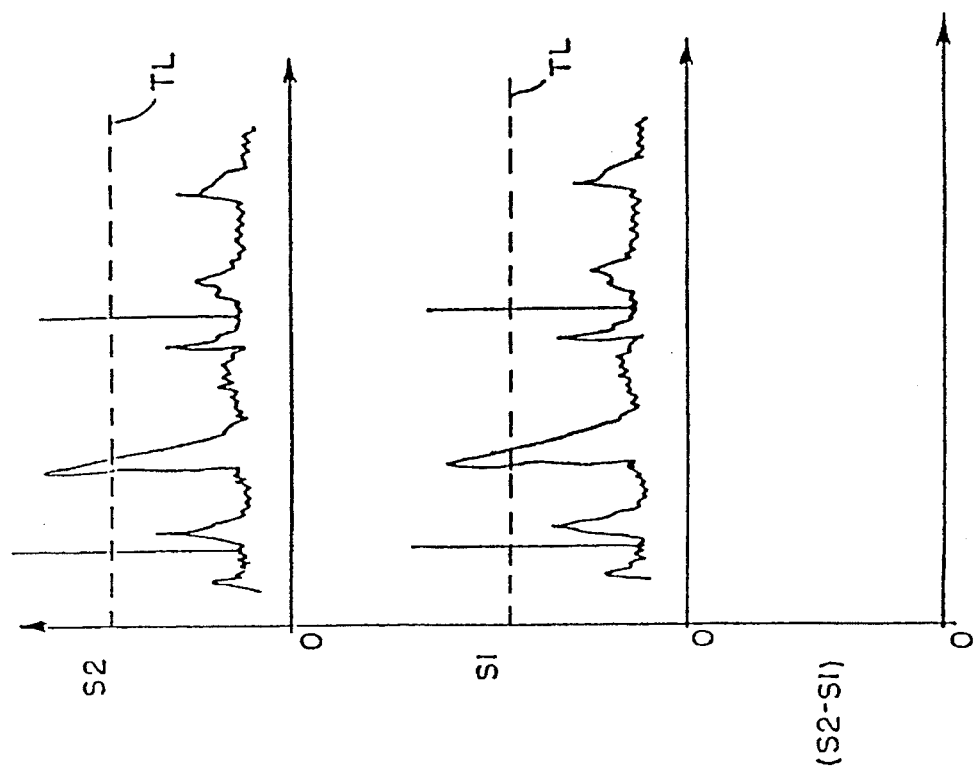
FIG. 6 illustrates graphs of signals detected and processed by the system of FIG. 3 for samples containing an unknown contaminant affected in a similar manner by heating in two different converters.

FIGS. 4–6 show amplitude vs. time graphs of signals output from detectors D1 and D2 for various substances to be detected. FIGS. 4–5 show signals with relatively high, time-varying backgrounds. Subtraction of signals produces a result (S2–S1) which is a positive (+) signal for detection of nitrogen compounds, and a negative (–) signal for detection of hydrocarbons, (olefins, are in diesel fuel or kerosene). The signal is positive for nitrogen containing compound detection (FIG. 4) because, at typical temperatures and flow rates employed, converter P1, which is ceramic, does not produce appreciable amounts of NO in the absence of nickel oxide. The signal (S2–S1) is negative for olefins (FIG. 5) because the signal S1 of detector D1 is larger than the signal S2 of detector D2 for at least two possible reasons. The first reason is that more signals related to olefin chemiluminescence are produced in the ceramic converter than in the nickel converter, and the second reason is that less of the chemiluminescence radiation produced in detector D1 is filtered out by the quartz filter of detector D1 than by the infrared filter of detector D2. In any event, a net negative signal (S2–S1) resulting from the subtraction is an indication of the presence of an olefin contaminant such as diesel fuel or kerosene.

Note that the signal (S2–S1) of FIG. 4 might be missed unless subtraction of signals is performed since the high level of background signals of S2 and S1 might permit the nitrogen compound signal to hide. Also, the importance of avoiding time shifts in flow through the converters P1, P2 and detectors D1, D2 is apparent, particularly for analysis under conditions where background levels vary rapidly and would not subtract to zero if time-shifting occurred.

The ceramic converter P1 apparently "cracks" the diesel fuel or kerosene to produce a double-bonded hydrocarbon, most probably an alkene such as 1-butane or propylene, which chemiluminescence with ozone ($O_3$). Apparently in the nickel containing converter P2, some of the cracked material burns or reacts to form non-chemiluminescing compounds before as much of the alkene is formed in the nickel containing converter P2 as in the ceramic converter P1. This theory would seem to explain the result that for gasoline which already contains alkenes, the alkenes are apparently unaffected in passing through the converters. In fact, the converters are usually not necessary to detect gasoline by chemiluminescence.

For gasoline contaminants the net signal (S2–S1) will typically be negative because the quartz filter of D1 attenuates less radiation than the infrared filter of D2.

In order to avoid missing other foreign substances such as chemicals from a cigarette in a container or sample being analyzed, the threshold levels of the individual signals S1 and S2 should be analyzed in addition to the net signal (S2–S1). See, for example, FIG. 6, in which it can be seen that for certain contaminants it's possible that subtraction of the signals S2 and S1 yields a net result of (S2–S1) nearly 0, even though each detector contains signal peaks which occur at a specified time (within a window relative to arrival of containers at the test station) and have a shape and amplitude which satisfy criteria for the presence of a contaminant. Thus if the peaks of the individual signals S1 and S2 are compared to threshold levels TL, the contaminant, such as cigarette residue, may be properly detected. The signals illustrated in FIG. 6 for S1 and S2, respectively, indicate such peaks and therefore the system would indicate a hit and produce an appropriate reject signal. The sharp spike-like signals of FIG. 6 and those of FIG. 7 (which are for analysis of a sample illustrated to lack contaminants of the type and quantity to be detected), though above the threshold level (TL), lack the necessary shape characteristics to indicate the presence of a contaminant.

Accordingly, the microprocessor controller 34 in accordance with the appropriate software provided for the method of the present invention, not only subtracts signal S1 from S2 to determine the presence or absence of certain hydrocarbons or nitrogen containing compounds, but may also look at the individual signals S1 and S2 to determine how the individual signals compare to the predetermined threshold criteria. The possibilities of various detection logic criteria are indicated in the following table.

Figure 7:
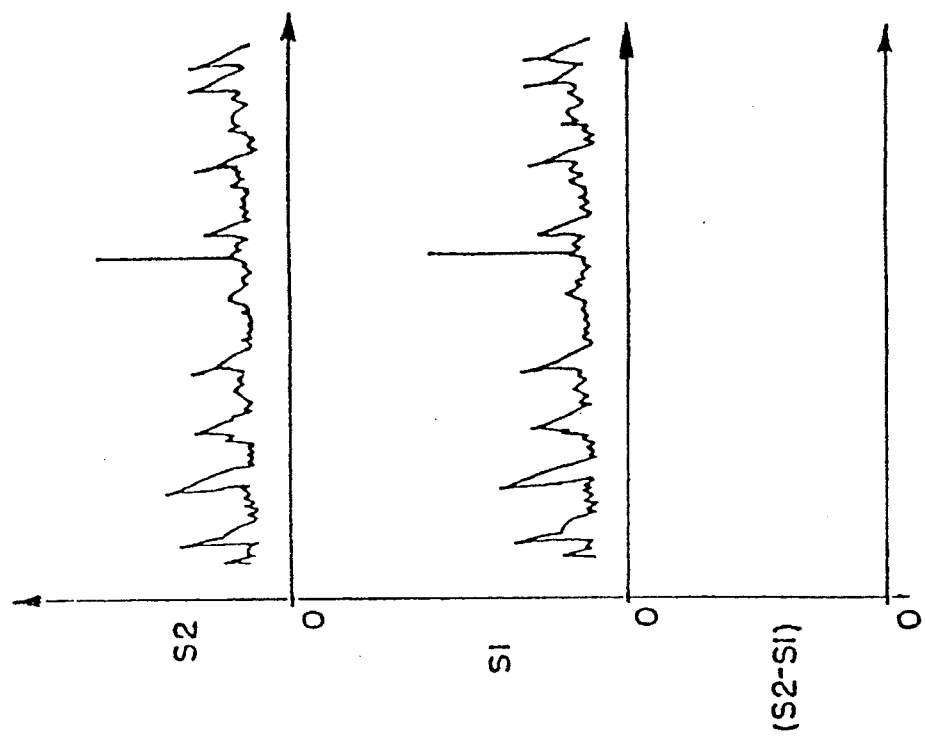
FIG. 7 illustrates graphs of signals detected and processed by the system of FIG. 3 for samples containing no contaminants of the type detectable by the present invention.

| | Detection By Net Signal | | |
|---|---|---|---|
| s2–s1 | Indicates Presence Of | Action | Drawing FIG. |
| + (above + threshold) | Nitrogen ($NH_3$) | Reject | FIG. 4 |
| − (below − threshold) | Diesel Fuel, Kerosene | Reject | FIG. 5 |
| 0 (but s1 and s2 otherwise show peak of specified character) | Cigarette or other Contaminants | Reject | FIG. 6 |
| 0 (and s1 or s2 (or both) lack peak of specified character) | No Contaminant | Accept | FIG. 7 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of detecting selected compounds in a sample by chemiluminescent gas phase reaction with a reactant comprising the steps of:

collecting the sample;

dividing the sample into first and second portions;

heating the first portion of the sample to a first predetermined temperature in a first pyrolyzer having first conversion properties with respect to the selected compounds;

heating the second portion of the sample to a second predetermined temperature in a second pyrolyzer having second conversion properties with respect to the selected compounds which are different from the first conversion properties of the first pyrolyzer;

mixing the heated first portion of the sample with the reactant to cause a chemical reaction therewith in order to generate radiation by chemiluminescence having characteristic wavelengths related to substances in said first portion;

mixing the heated second portion of the sample with the reactant to cause a chemical reaction therewith in order to generate radiation by chemiluminescence having characteristic wavelengths related to substances in said second portion;

selectively detecting radiation emitted by chemiluminescence from a selected compound in the first portion of the sample;

selectively detecting radiation emitted by chemiluminescence from conversion of the selected component in the second portion of the sample and at least the same compound in the first portion of the sample in the second portion of the sample;

generating first electrical signals from the radiation selectively detected from the first portion of the sample and second electrical signals from the radiation selectively detected from the second portion of the sample; and comparing the first electrical signals with the second electrical signals in order to determine the presence or absence of selected compounds in the sample;

wherein said heating, mixing, detecting, and generating steps are performed at substantially the same times for said first portion as for said second portion and wherein the step of comparing includes the steps of comparing the first electrical signals and the second electrical signals so as to cancel signals related to said portions of background components.

2. The method of claim 1 wherein said first pyrolyzer is formed from ceramic materials and the second pyrolyzer is formed from nickel materials.

3. The method of claim 1 including the further steps of comparing each of the first and second electrical signals individually with second predetermined threshold criteria.

4. The method of claim 1 wherein said dividing step is performed in a manner to yield substantially equal portions of the sample.

5. The method of claim 1 wherein said heating steps performed in said first and second pyrolyzers such that each is heated to substantially the same temperature in the range of about 800° to 1000° C.

6. The method of claim 1 wherein the result of the comparing step is further compared to a first predetermined threshold criteria.

7. A system for detecting selected compounds in a sample by chemiluminescent gas phase reaction with a reactant comprising:

means for collecting the sample;

means for dividing the sample into first and second portions;

first converter means for hearing the first portion of the sample to a first predetermined temperature, said first converter means having first conversion properties with respect to the selected compounds;

second converter means for heating the second portion of the sample to a second predetermined temperature, said second converter means having second conversion properties with respect to the selected compounds which are different from the first conversion properties of the first converter means;

means for mixing the heated first portion of the sample with the reactant to cause a chemical reaction therewith in order to generate radiation by chemiluminescence having characteristic wavelengths related to substances in said first portion;

means for mixing the heated second portion of the sample with the reactant to cause a chemical reaction therewith in order to generate radiation by chemiluminescence having characteristic wavelengths related to substances in said second portion;

means for selectively detecting radiation emitted by chemiluminescence from a selected compound of the first portion of the sample;

means for selectively detecting radiation emitted by chemiluminescence from the conversion of selected compounds and at least the same compound in the first portion in the second portion of the sample;

means for generating first electrical signals having amplitudes and durations related to the detected characteristic wavelengths of radiation emitted from the mixed first portion of the sample and second electrical signals having amplitudes and durations related to the detected characteristic wavelengths of radiation emitted from the mixed second portion of the sample; and means for comparing the first electrical signals with the second electrical signals in order to determine the presence or absence of selected compounds in the sample;

said heating, mixing, detecting, and generating means being operable to process said first portion at substantially the same relative times as the processing of said second portion to thereby permit cancellation of signals related to background components from said first and second electrical signals by said comparing means.

8. The system of claim 7, wherein the first converter means has a heating chamber including ceramic materials and the second converter has a heating chamber including nickel materials.

9. The system of claim 7 wherein the means for comparing is operable to subtract the first electrical signals from the second electrical signals and to compare the net result to predetermined threshold criteria.

10. The system of claim 9 further including means for comparing each of the first and second electrical signals individually with predetermined threshold criteria.

11. A method of detecting selected compounds in a sample by chemiluminescent gas phase reaction of a compound which might be present as a background component of the sample, and as a converted product of one of said selected compounds, with a chemical reactant comprising the steps of:

collecting the sample;

dividing the sample into first and second portions;

heating the first portion of the sample to a first predetermined temperature in a first pyrolyzer having a first conversion properties such that no appreciable amounts of the compound in the background component can be produced thereby conversion of the selected components;

heating the second portion of the sample to a second predetermined temperature in a second pyrolyzer having second conversion properties such that the measurable amounts of the compound from the background component, and also from converted products of the selected compounds can be produced;

mixing the heated first portion of the sample with said chemical reactant to cause a chemical reaction therewith in order to generate radiation by chemiluminescence having characteristic wavelengths related to a compound of the background component in said first portion;

mixing the heated second portion of the sample with said chemical reactant to cause a chemical reaction therewith in order to generate radiation by chemiluminescence having characteristic wavelengths related to the background component of the compound, and the compound produced by conversion of the selected compounds in said second portion;

selectively detecting radiation emitted by chemiluminescence from the background component in the first portion of the sample;

selectively detecting radiation emitted by chemiluminescence from the converted products of the selected compounds in the second portion of the sample as well as said background components in the second portion;

generating first electrical signals from the radiation selectively detected from the first portion of the sample and second electrical signals from the radiation selectively detected from the second portion of the sample; and comparing the first electrical signals with the second electrical signals in order to determine the presence or absence of selected compounds in the sample;

wherein said heating, mixing, detecting, and generating steps are performed at substantially the same times for said first portion as for said second portion and wherein the step of comparing includes the steps of comparing the first electrical signals with the second electrical signals so as to cancel signals related to said compound in the background component in said portions.

12. The method of claim 11 wherein said first pyrolyzer is formed from ceramic materials and said second pyrolyzer is formed from nickel materials.

13. The method of claim 11 including the further steps of comparing each of the first and second electrical signals individually with second predetermined threshold criteria.

14. The method of claim 11 wherein said dividing step is performed in a manner to yield substantially equal portions of the sample.

15. The method of claim 11 wherein said heating steps are performed in first and second converters each heated to substantially the same temperature in the range of about 800° to 1000° C.

16. The method of claim 11 wherein the result of the comparing step is further compared to a first predetermined threshold criteria.

* * * * *